United States Patent [19]

Newman

[11] Patent Number: 5,057,430
[45] Date of Patent: Oct. 15, 1991

[54] BIOCHEMICAL SENSOR RESPONSIVE TO BUBBLES

[75] Inventor: Arnold L. Newman, Kensington, Md.

[73] Assignee: Biotronic Systems Corporation, Rockville, Md.

[21] Appl. No.: 244,677

[22] Filed: Sep. 15, 1988

[51] Int. Cl.$^5$ ............................................... C12M 1/40
[52] U.S. Cl. .................................. 435/288; 435/291; 435/817; 204/403
[58] Field of Search ....................... 435/4, 7, 288, 291, 435/817, 807; 422/80, 68, 98, 90, 69; 436/518, 528, 531, 532, 525, 806, 807; 204/403; 324/60 C, 61 R, 61 P, 71.1, 71.5

[56] References Cited

U.S. PATENT DOCUMENTS

| | | |
|---|---|---|
| 3,350,941 | 11/1967 | Misevich et al. |
| 3,817,837 | 6/1974 | Rubenstein et al. |
| 4,057,823 | 11/1977 | Burkhardt et al. |
| 4,184,952 | 1/1980 | Stewart |
| 4,203,087 | 5/1980 | Kovac et al. |
| 4,214,203 | 7/1980 | Coster et al. |
| 4,219,335 | 8/1980 | Ebersole ........................ 436/806 X |
| 4,240,028 | 12/1980 | Davis, Jr. |
| 4,247,299 | 1/1981 | Klein et al. |
| 4,335,379 | 6/1982 | Martin |
| 4,384,936 | 5/1983 | Obana ........................... 435/817 X |
| 4,423,337 | 12/1983 | Senturia et al. |
| 4,444,892 | 4/1984 | Malmros ....................... 436/806 X |
| 4,453,126 | 6/1984 | Volgyesi |
| 4,517,547 | 5/1985 | Gray et al. |
| 4,571,154 | 2/1986 | Raymond et al. |
| 4,728,882 | 3/1988 | Stanbro ......................... 204/400 X |
| 4,778,769 | 10/1988 | Forrest .......................... 435/817 X |
| 4,780,191 | 10/1988 | Romette ........................ 435/817 X |
| 4,822,566 | 4/1989 | Newman ....................... 435/817 X |
| 4,839,017 | 6/1989 | Taniguchi ...................... 435/817 X |

OTHER PUBLICATIONS

Maggio (editor), Enzyme-Immunoassay, CRC Press, Boca Raton, Florida, 1980, pp. 106-110 and 231-236.

"The Incremental Ohmic Resistance Caused by Bubbles Adhering to an Electrode", H. Vogt, Journal of Applied Electrochemistry 13 (1983) pp. 87-88.

"Systematic Errors in Conductimetric Instrumentation Due to Bubble Adhesions on the Electrodes: An Experimental Assessment", P. S. Neelakantaswamy et al, Rev. Sci. Instrum., vol. 56, No. 2, Feb. 1985, pp. 303-306.

Primary Examiner—David L. Lacey
Assistant Examiner—William H. Beisner
Attorney, Agent, or Firm—Kerkam, Stowell, Kondracki & Clarke

[57] ABSTRACT

A biochemical analyte sensor comprises a pair of electrical conductors in a fluid environment. Between the conductors is a surface of silicone rubber, for instance. An enzyme/substrate combination causes molecules of a volatile material to be produced in the fluid. The volatile material nucleates as bubbles near the surface of the sensor. The bubbles displace molecules of the fluid from the surface and drastically alter the dielectric properties on or near the sensor surface.

15 Claims, 6 Drawing Sheets

FIG. 1
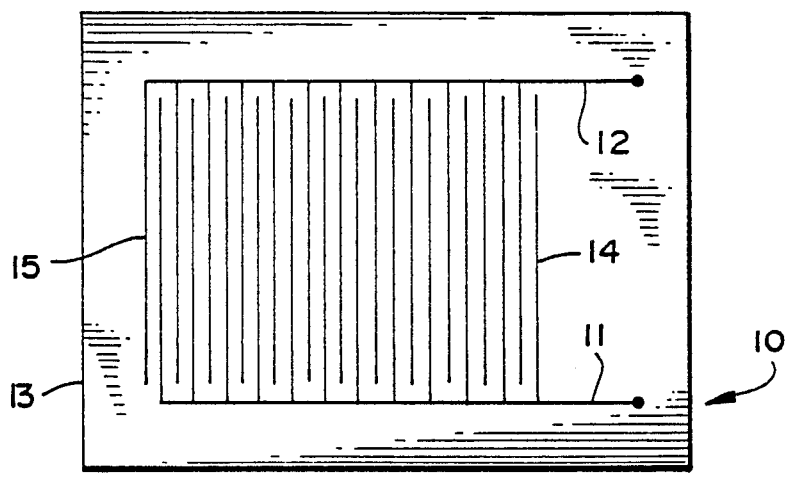
FIG. 2
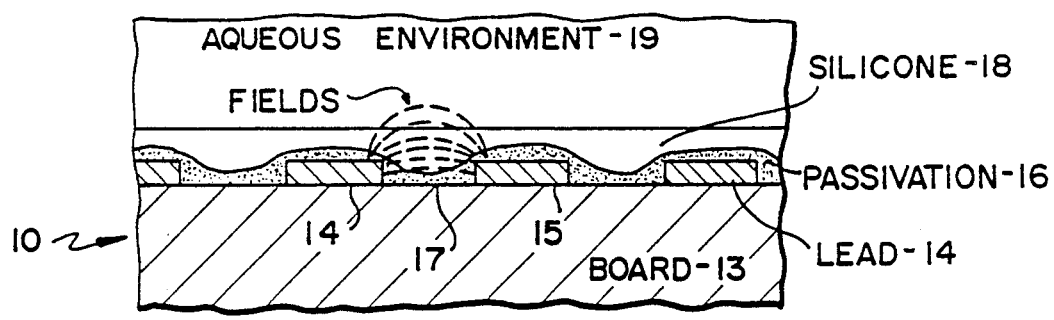
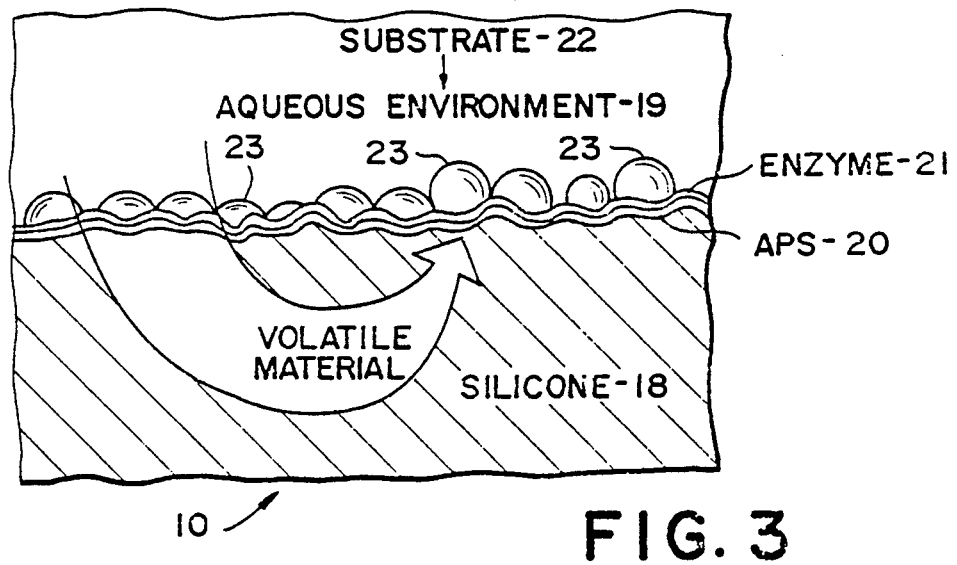
FIG. 3

BIOCHEMICAL SENSOR RESPONSIVE TO BUBBLES

FIELD OF THE INVENTION

This invention relates to a bi sensor, and more specifically relates to a sensor using a combination of an enzyme and a substrate for detecting the presence of analytes in a solution.

BACKGROUND OF THE INVENTION

Capacitive affinity sensors have been used to measure the concentration of an analyte by detecting a change in capacitance as molecules move in or out of an electric field between two electrodes of the sensor, for instance. The movement of molecules onto and off of the surface changes the dielectric properties of a biochemically active layer between the two electrodes. The displacement of the solvent molecules by the moving molecules reduces the measured capacitance between the two electrodes. The capacitance between the two electrodes changes in relation to the concentration of the analyte being measured by such a sensor, for instance. Such capacitive affinity sensors, however, have a sensitivity limited by the amount of water displaced from the sensor surface by normal biomolecules.

U.S Pat. No. 4,728,882 to Stanbro et al. describes a capacitive sensor for determining the presence of volatile materials such as hydrocarbons in a liquid medium. The sensor of that patent includes a concentrating layer of room temperature vulcanized (RTV) silicone rubber having a high affinity for non-polar molecules. Hydrocarbon molecules are non-polar and readily enter the surface of the concentrating layer of silicone rubber. As a result, bubbles nucleate on the surface of the concentrating layer of silicone rubber in proportion to hydrocarbon concentration with a corresponding reduction in capacitance of the sensor. The sensor of the Stanbro et al. Patent measures an amount of molecules of a volatile material, but does not include a means for generating molecules of such a volatile material. The sensor of the Stanbro et al. Patent is, therefore, not as versatile as the present inventor's biochemical sensor. The present inventor is a co-inventor of the Stanbro et al. Patent.

U.S. Pat. No. 3,817,837 to Rubenstein et al. describes a method for assaying concentrations of organic materials according to enzymatic activity. An amplification is obtained by forming a large number of molecules in the presence of one molecule. This patent also describes specific methods of assaying for an enzyme, including the use of ion specific electrodes. No mention is made, however, of nucleated bubbles, of a surface upon which bubbles might nucleate, or of a sensor that responds to such nucleated bubbles.

A need exists for a biochemical sensor that has an increased sensitivity facilitated by a bubble mechanism, where a volatile material is generated that nucleates as bubbles and comes out of solution into the gas phase at the surface of the sensor.

SUMMARY OF THE INVENTION

The invention concerns an apparatus for responding to an analyte comprising a means for producing volatile molecules, a surface comprising a means for nucleating bubbles from the volatile molecules, and a means for responding to the bubbles that nucleate on the surface.

One embodiment comprises a sensor having a surface of silicone between a pair of electrical conductors and an enzyme and a substrate that produce a volatile material. For example, the enzyme catalase and the substrate $H_2O_2$ produce water and the volatile material $O_2$. The volatile material is capable of being nucleated as bubbles at the silicone surface. Nucleated bubbles quickly and dramatically change the dielectric properties of the sensor according to the concentration of the analyte.

BRIEF DESCRIPTION OF THE FIGURES

FIG. 1 shows a top view of a capacitive sensor.

FIG. 2 shows an enlarged cross-sectional view of the FIG. 1 sensor.

FIG. 3 shows a detail of the view of FIG. 2.

FIG. 4b shows a reference sensor surface which is used in comparison with the sensor of FIG. 4a.

FIG. 5b shows a reference sensor surface which is used in comparison with the sensor of FIG. 5a.

DETAILED DESCRIPTION OF THE FIGURES

Figure 4A:
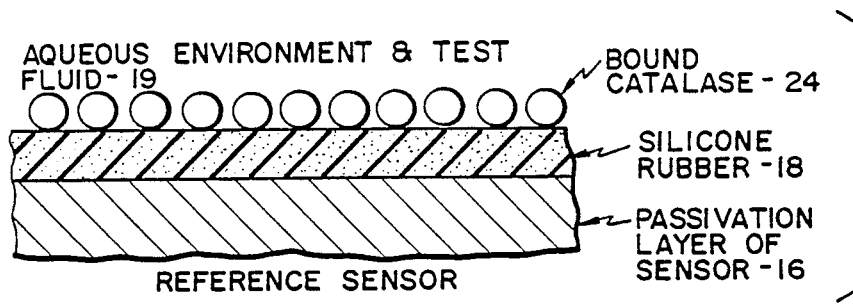
FIG. 4a shows an embodiment of a test sensor surface of this invention.

FIGS. 1, 2, and 3 illustrate the principle of this invention.

FIG. 1 shows a top view of a capacitive sensor 10 comprising two electrodes 11 and 12 supported on a chip surface 13. The electrodes have interdigitated leads 14 and 15. Capacitance between these two electrodes 11 and 12 is determined by the dielectric properties of a material between and above these electrodes. Capacitance is proportional to the ratio of the dielectric constant of the material to the distance between the electrodes 11 and 12. Total capacitance between the electrodes 11 and 12 depends on the component capacitances of layers covering electrodes 11 and 12 as well, as described in U.S. patent application, Ser. No. 044,761, now abandoned, for Three Dimensional Binding Site Array For Interfering With An Electrical Field, filed May 1, 1987 and assigned to the same assignee as this invention. The specification of Ser. No. 044,761 is incorporated by reference.

FIG. 2 shows an enlarged cross section of the capacitive sensor 10 of FIG. 1. The interdigitated leads 14 and 15 of the two electrodes 11 and 12 are spaced from one another. A passivation layer 16 covers each lead 14 and 15 of both electrodes 11 and 12 and the portion 17 of the chip 13 which is exposed between the leads. A surface 18 of RTV silicone rubber (GE 118), for instance, covers the passivation layer 16. The chip 13, leads 14 and 15, passivation layer 16 and silicone rubber surface 18 comprise a sensor surface. Deposition of such a passivation layer and silicone rubber surface are described in U.S. Pat. No. 4,728,882 for Capacitive Chemical Sensor For Detecting Certain Analytes, Including Hydrocarbons In A Liquid Medium, to Stanbro et al., the specification of which is incorporated by reference.

An aqueous environment 19 comprising phosphate buffered saline (PBS) covers the sensor surface. In this case, the passivation layer 16, silicone rubber surface 18, and aqueous environment 19 compose a dielectric material between the two electrodes 11 and 12 of the capacitive sensor 10. This dielectric material influences electric fields that are produced when an electric potential is applied across the two electrodes 11 and 12.

The silicone rubber surface is permeable and has many irregularities. The silicone rubber surface provides a mechanism through which a volatile material comes out of solution into a gas phase and enables an electrode 11 or 12 of the sensor to carry a signal in response to the enzyme and substrate activity. U.S. Pat. No. 4,728,882, mentioned above, describes this mechanism provided by the silicone rubber surface 18.

According to the present invention, a volatile material is provided adjacent the silicone rubber surface 18, where the volatile material nucleates as bubbles. In this manner, the dielectric properties of the material drastically change between the two electrodes 11 and 12 and capacitance of the sensor 10 changes according to the concentration of an analyte, for instance.

FIG. 3 shows an enlarged detail of the surface 18 comprising the silicone rubber. According to one embodiment of this invention, APS (3-aminopropyltriethoxy silane) 20 covers the layer of silicone rubber 18. APS 20 covalently binds and immobilizes a layer of an enzyme 21 to the silicone layer. APS is not necessary when the enzyme 21 is immobilized by adsorption onto the silicone layer 18. These immobilized enzyme molecules remain attached and stationary in the presence of any other biochemistry. The thickness of the layer of enzyme 21 is actually very small compared to the irregularities in the surface of the silicone rubber 18, but for clarity the thickness of the layer of enzyme 21 is exaggerated in FIG. 3. Though FIG. 3 shows continuous layers of silicone rubber 18, APS 20, and enzyme 21, these layers can be made discontinuous. For example, the silicone rubber surface 18 may be deposited as a grid pattern containing APS within elements of the grid.

A substrate 22 to the enzyme 21 is added to the aqueous environment 19 covering the sensor surface 10. The substrate 22, in the presence of the enzyme 21, is transformed into a volatile material, for instance. The silicone rubber 18 is a surface in which the volatile material is capable of coming out of solution into the gas phase. Accordingly, bubbles 23 nucleate on the sensor surface.

The inventor has found that the presence of nucleated bubbles at the sensor surface drastically alters the dielectric properties of the sensor compared to an absence of nucleated bubbles at the sensor surface. The gas bubbles 23 on the sensor surface displace molecules of the aqueous environment 19 from the sensor surface. As a result, there is a phase change at the sensor surface and within the components of the dielectric material. Specifically, liquid molecules comprising the aqueous environment 19 over the silicone rubber 18 are displaced by gas bubbles 23 when the bubbles nucleate. The gas bubbles 23 have a dielectric constant of 1-3 and the aqueous environment 19, comprising water and PBS, has a dielectric constant of over 78. This displacement of water by gas bubbles within the dielectric material drastically changes the dielectric properties of that material and thus the capacitance between the two electrodes 11 and 12.

FIG. 4a shows a sensor, which had been covered by a passivation layer 16, dipped in 1% RTV silicone rubber (GE RTV 118, for instance) solution in acetone and allowed to cure overnight to form the silicone rubber layer 18. The enzyme catalase 24 is adsorbed or covalently bound to the silicone rubber 18. An aqueous environment 19 and test fluid covers the silicone rubber 18 and the immobilized catalase 24.

Figure 4B:
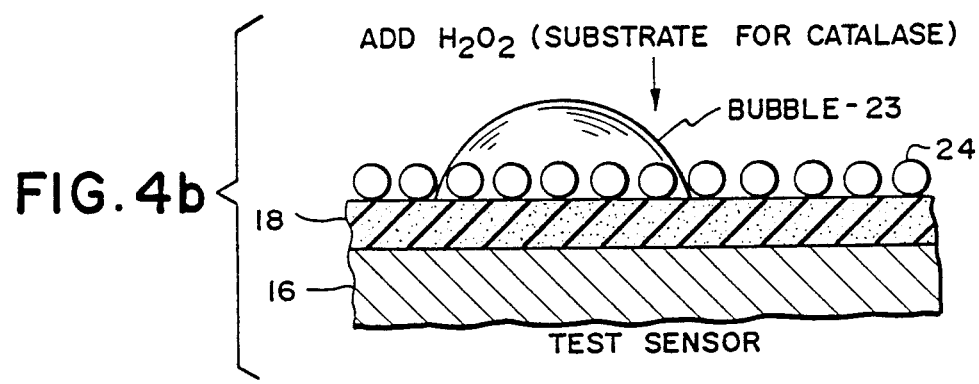

FIG. 4b illustrates the addition of $H_2O_2$ to the aqueous environment 19 covering the sensor 10 of FIG. 4a. $H_2O_2$ is a substrate for the enzyme catalase 24. A substrate of an enzyme is the material upon which the enzyme acts as a catalyst. In this case, catalase 24 chemically converts molecules of $H_2O_2$, which are near the sensor surface, to $O_2$ and water. $O_2$ is a volatile material capable of nucleating or coming out of solution into the gas phase on or near the sensor surface, and any bubbles already existing on the sensor surface grow as $O_2$ enters the gas phase. The nucleated bubbles 23 comprise localized, high concentrations of $O_2$, which result when uninhibited catalase catalyzes $H_2O_2$ to form $O_2$ and water. Such bubbles 23 displace molecules of the aqueous environment 19 from the sensor surface. The displacement of these molecules by the bubble 23 drastically changes dielectric properties on or near the sensor surface. A comparison of the output of the reference sensor with that of the test sensor indicates the concentration of $H_2O_2$ in the aqueous environment 19, for instance. The preparation and testing of the sensors of FIGS. 4a and 4b is described below concerning Experiment I and FIG. 9. In this experiment, 90% of the count increase occurs in 1-2 minutes and indicates that capacitance changed 30 pf in that time, approximately.

Figure 5A:
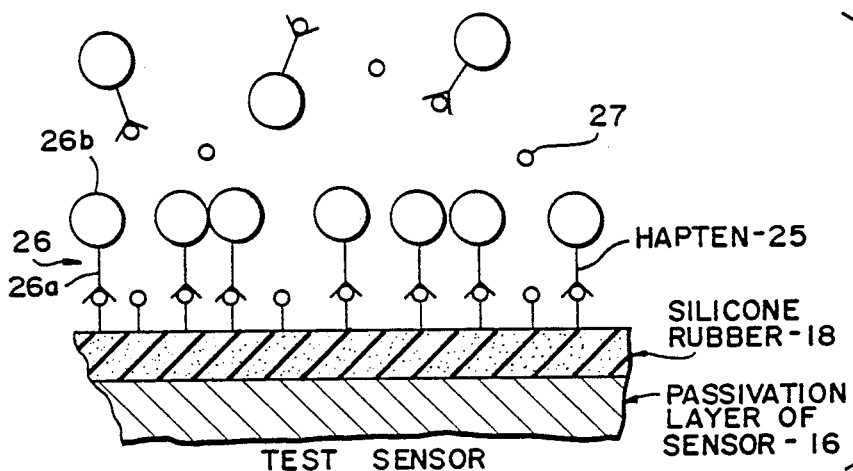
FIG. 5a shows a competitive embodiment of a test sensor surface of this invention.
Figure 5B:
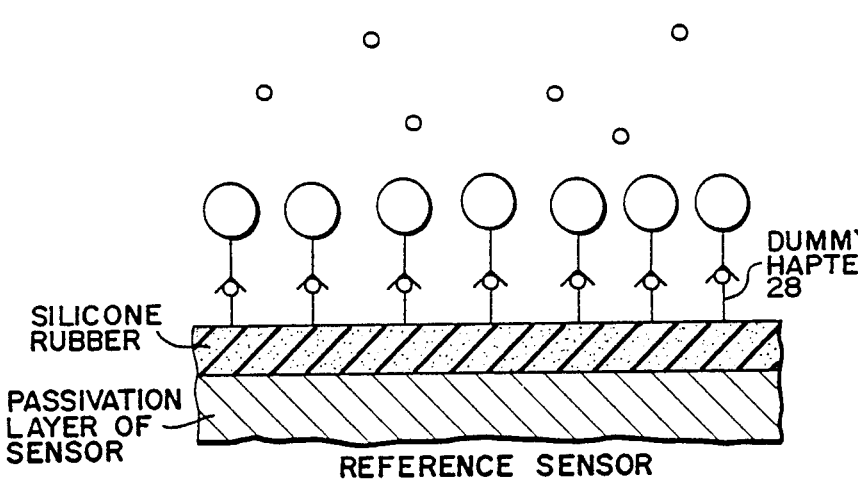

FIGS. 5a and 5b show a competitive embodiment of the invention. FIG. 5a shows a test sensor surface having a layer of immobilized hapten 25 or antigen, which is adsorbed or covalently bound to the silicone rubber 18. An enzyme-antibody conjugate 26 is introduced into the aqueous environment 19 and binds to the hapten 25 or antigen, because the antibody 26a is biospecific to the hapten 25 or antigen. Free hapten 27 is introduced into the aqueous environment 19. The free hapten 27 competitively displaces the enzyme-antibody conjugate 26 from the hapten 25 on the sensor surface. Thus, the amount of enzyme 26b, such as catalase, decreases near and on the sensor surface. When the substrate $H_2O_2$ is added to the test fluid, fewer bubbles form than before the free hapten 27 was added, because less enzyme 26b is present near or on the sensor surface.

FIG. 5b shows a reference sensor surface, which is used in a comparison with the competitive sensor of FIG. 5a. The referenced sensor comprises a layer of dummy hapten 28. The enzyme-antibody conjugate cannot be displaced by free hapten 27 from the dummy hapten 28. The formation of bubbles by this reference sensor remains at a maximum when $H_2O_2$ is added, because there is no displacement of the enzyme-antibody conjugate 26 by the free hapten 27. A comparison of the maximum of the reference sensor surface with that of the test sensor surface of FIG. 5a indicates the concentration of an antibody in a test fluid, for instance. The following biochemical binding systems can be used in a competitive binding embodiment to test for particular analytes.

| Biochemical Binding Systems | | |
| --- | --- | --- |
| immobilized analyte | binding agent | Analytes |
| antigen | antibody | antigen |
| hapten | antibody | hapten |
| polysaccharides | lectin | polysaccharides |
| glycoproteins | lectin | glycoproteins |
| glycolipids | lectin | glycolipids |
| enzyme inhibitor | enzyme | enzyme inhibitor |
| enzyme inhibitor | enzyme | enzyme substrate |
| neurotransmitters | neural receptor | neurotransmitters |
| hormones | neural receptor | hormones |

Figure 6A:
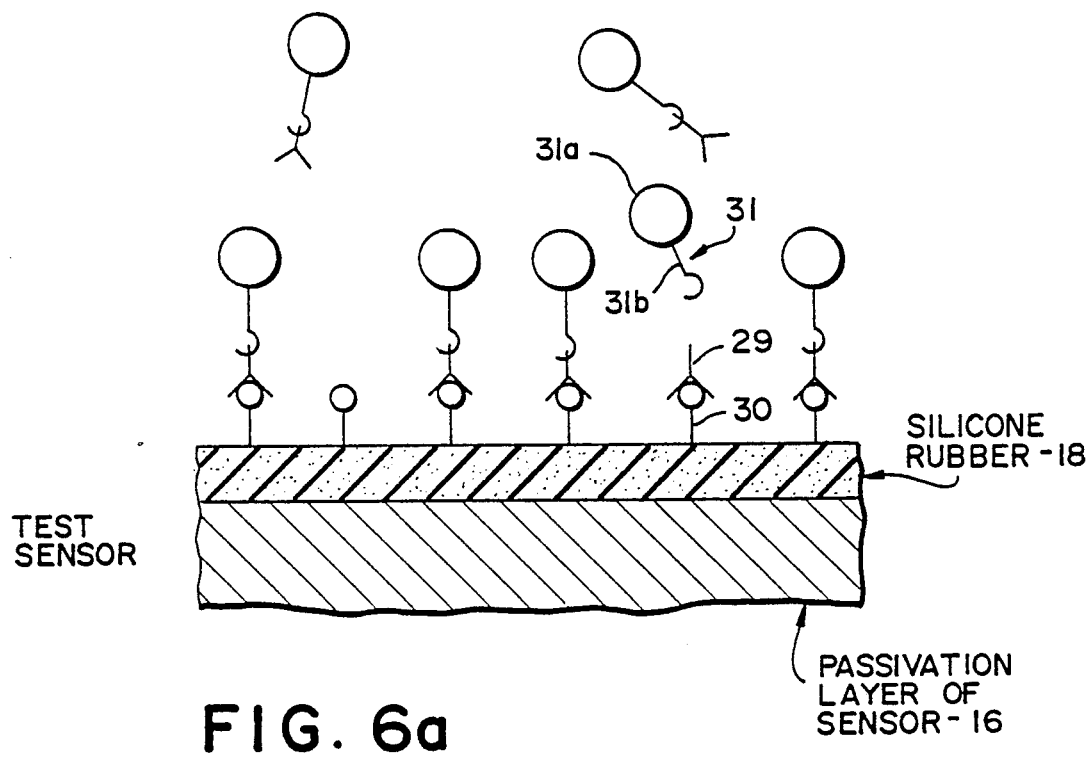
FIGS. 6a and 6b show another embodiment of this invention.

FIG. 6a shows another embodiment of a test sensor surface of this invention. A human antibody 29 contained in the test fluid binds to a layer of antigen 30, which is adsorbed or covalently bound to the silicone rubber 18, on the sensor surface. Such a human antibody 29 is the HIV antibody in blood. A fluid containing an enzyme-protein conjugate 31 is mixed with the test fluid. The enzyme-protein conjugate 31 binds to the human antibody 29. Some of the human antibodies 29 bind to the antigen 30 on the sensor surface, bringing the conjugated enzyme 31 close to the sensor surface. The enzyme 31a catalyzes added $H_2O_2$ to form water and a bubble of $O_2$ on the sensor surface. An antibody to the human antibody 29 can be conjugated to the enzyme 31a instead of the protein 31b. The protein 31b is a generic antibody-binding protein, such as Protein G or Protein A.

Figure 6B:
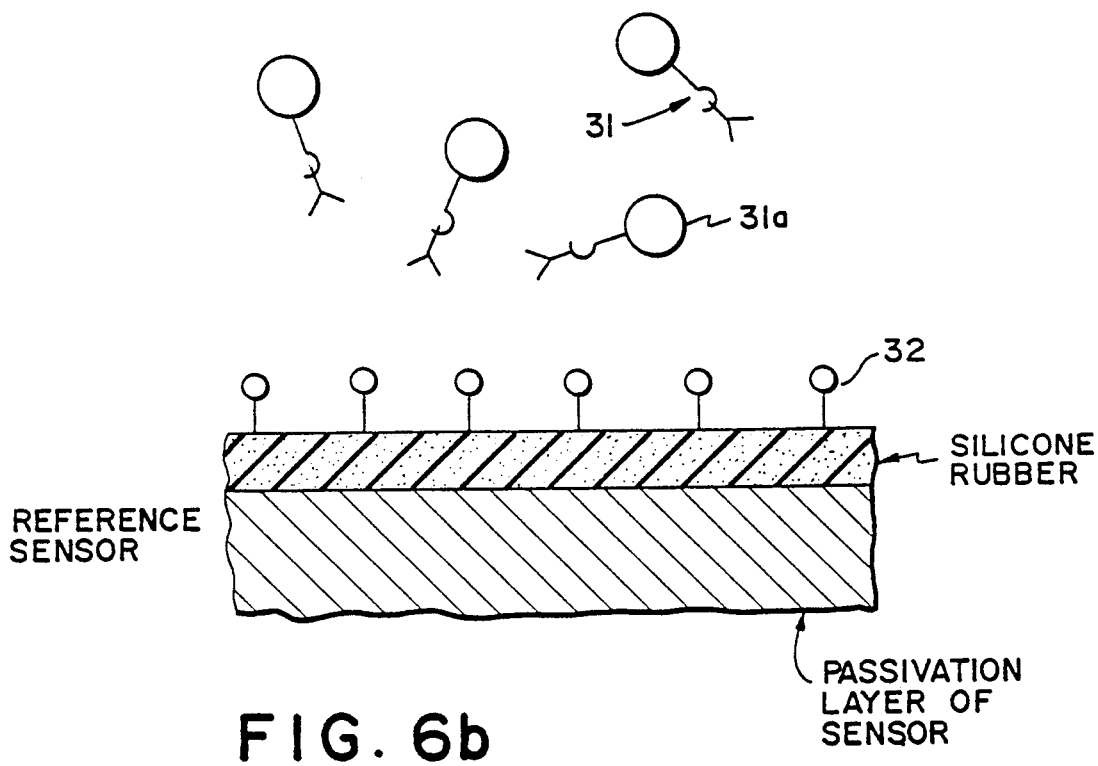

FIG. 6b shows a reference sensor surface which is used in comparison with the sensor of FIG. 6a. A nonsense antigen 32 (i.e., an antigen non-reactive with HIV antibodies) is placed on the sensor surface. Specific binding does not occur between this nonsense antigen 32 and the human antibodies 29. The formation of bubbles at the surface of this reference sensor remains at a minimum, because substantially no enzyme 31a specifically binds near the sensor surface. The sensor of FIG. 6a is compared with the sensor of FIG. 6b. When $H_2O_2$ is added, the sensor surface of FIG. 6a, having localized catalase, forms bubbles and a change occurs in the dielectric properties of the capacitive sensor. The sensors of FIGS. 6a and 6b were prepared and tested as described below concerning Experiment II and FIG. 10. In this experiment, 90% of the count increase occurs in 1-2 minutes and indicates that capacitance changed 10 pf in that time, approximately.

Figure 7A:
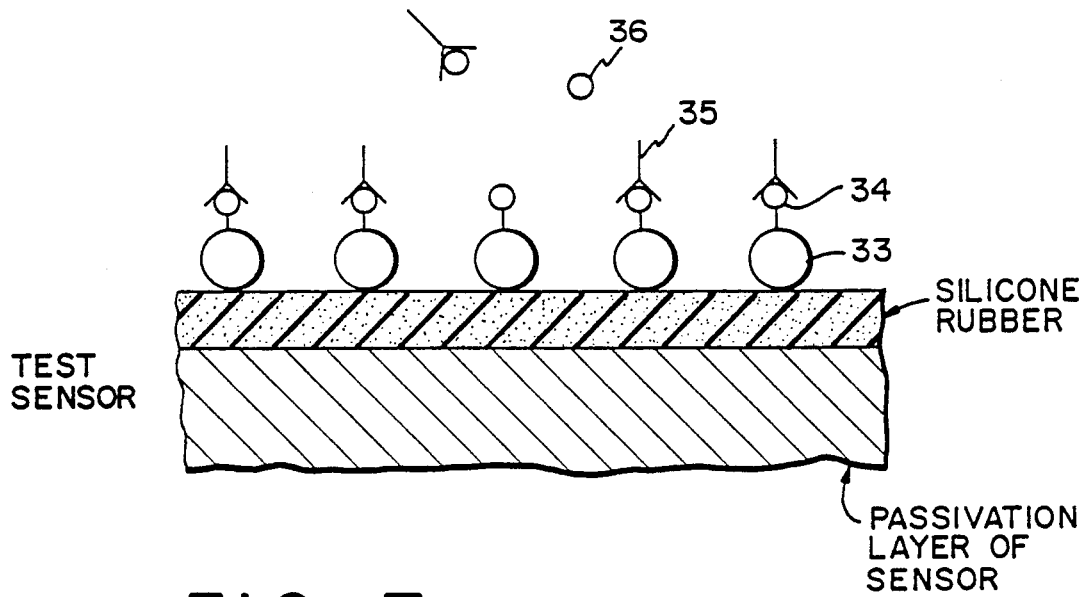
FIG. 7a and 7b show another embodiment of this invention.

FIG. 7a shows another embodiment of a test sensor surface of this invention. Enzyme 33 is adsorbed or covalently bound to the silicone rubber 18 on the sensor surface. Hapten 34 is covalently bound to the surface of the immobilized enzyme 33. An antibody 35 in the test fluid binds to the hapten 34 and inhibits the enzyme 33 by steric hindrance. Steric hindrance is an interference in the enzyme's catalytic activity due to physical interaction between the antibody 35 and the enzyme 33. When free hapten 36 is introduced into the test fluid, the free hapten 36 competitively displaces the antibody 35 from the immobilized hapten 34. Thus, the inhibition of the enzyme 33 is removed and the enzyme 33 can catalyze the $H_2O_2$ to form a bubble of $O_2$ on or near the sensor surface.

Figure 7B:
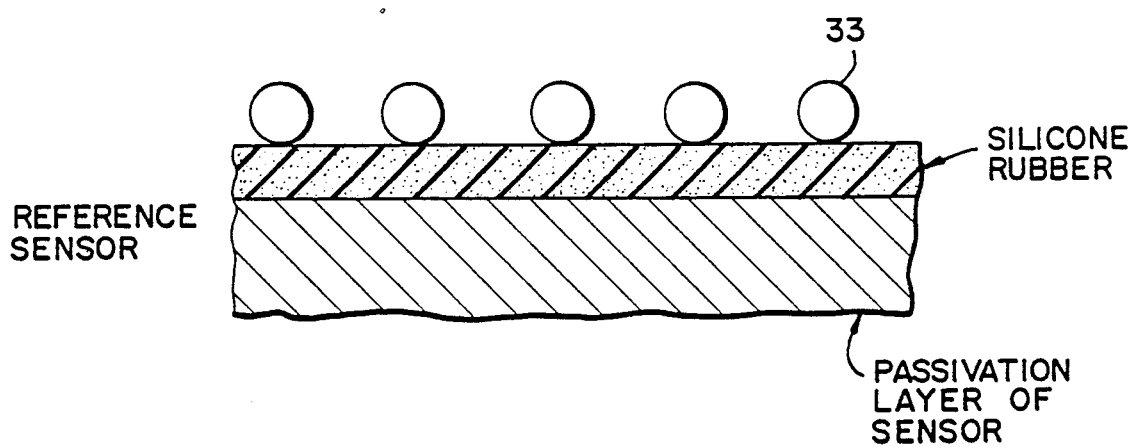

FIG. 7b shows a reference sensor surface which is used in comparison with the sensor of FIG. 7a. An enzyme 33, without hapten 34, is immobilized on the sensor surface. In this case, there is no inhibition of the enzyme 33 and a maximum of bubbles are produced at the sensor surface. The amount of bubbles nucleated by the enzyme 33 is inversely proportional to the amount of antibodies bound to the immobilized hapten 34 on the enzyme 33. Thus, a comparison of the capacitance in the absence and presence of nucleated bubbles indicates the concentration of the antibody and thus the free hapten, for instance. In another version, the reference sensor could have no chemistry on its surface and a minimum of bubbles are produced. The activity of the enzyme can be modulated, as described in U.S. Pat. 3,817,837 for Enzyme Amplification Assay, to Rubenstein et al. The sensors of FIGS. 7a and 7b show how the technique U.S. Pat. No. 3,817,837 would be implemented with the sensor of the present invention.

Figure 8:
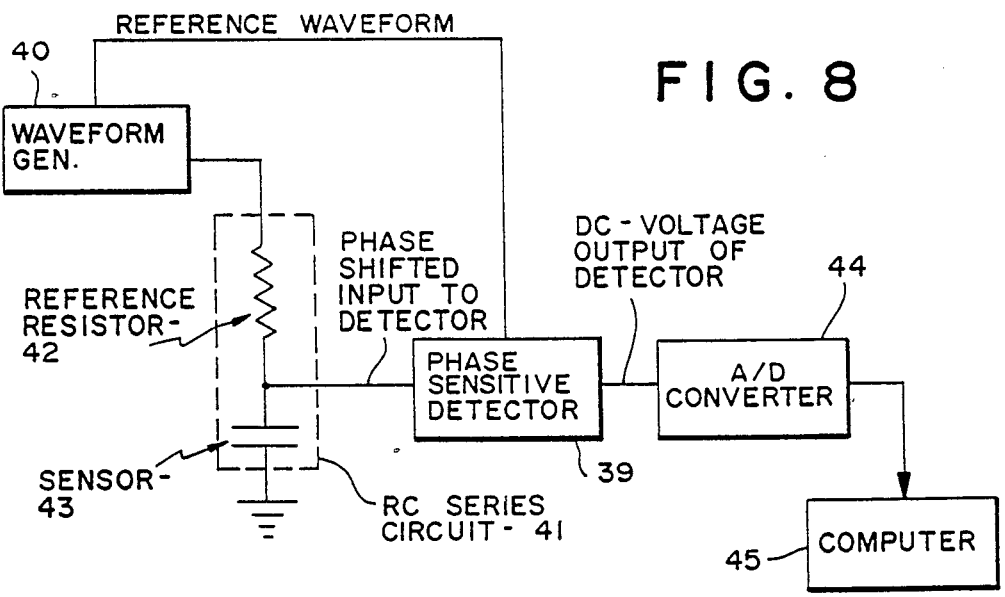
FIG. 8 illustrates an apparatus used in testing the sensors of this invention.

FIG. 8 illustrates an apparatus used by the inventor in making measurements with the sensor of this invention. Measurements were made with a phase sensitive detector circuit 39 that compares the phase and amplitude difference between a reference waveform from a waveform generator 40 and a waveform derived from the center tap of a simple RC series network 41, where the resistor 42 is chosen as a known reference impedance and the capacitor 43 is the sensor. The resistor's value is approximately equal to the nominal capacitive reactance of the sensor. Changes in the sensor's capacitance cause phase and amplitude changes to which the phase sensitive detector circuit 39 is responsive. The output of the phase sensitive detector circuit 39 is a DC voltage proportional to the phase and amplitude changes caused by the sensor 43. The DC voltage is fed into an analog-to-digital (A/D) converter 44 which provides a digital number to a computer 45. This digital number is plotted as the Y-axis on the experiment graphs. The number increases when the capacitance of the sensor 43 decreases.

EXPERIMENT I

Detection of $H_2O_2$ with a Biosensor Having Immobilized Catalase

Two tantalum pellets were anodized first at constant current up to a voltage of 120 volts, and then at a constant voltage of 120 volts for 1 hour. In this manner, each tantalum pellet is provided with a passivation layer as described in U.S. Pat. No. 4,769,121 for Sintered Pellet With Biochemically Active Layer, to A. Newman, the specification of which is incorporated by reference. The pellets were epoxied to a piece of plastic and maintained at a constant separation of approximately 3mm. Next, the pellets were dipped in a 10% solution of silicone (GE RTV 118) in acetone and allowed to cure overnight. Finally, the pellet assembly was soaked in 2 ml of PBS containing 450 $\mu$g of catalase.

Excess catalase was removed by soaking the tantalum pellets in PBS for 1 hour at room temperature. The tantalum pellet assembly was then placed in 2 ml of PBS and connected to the phase sensitive detector. $H_2O_2$ was added.

Figure 9:
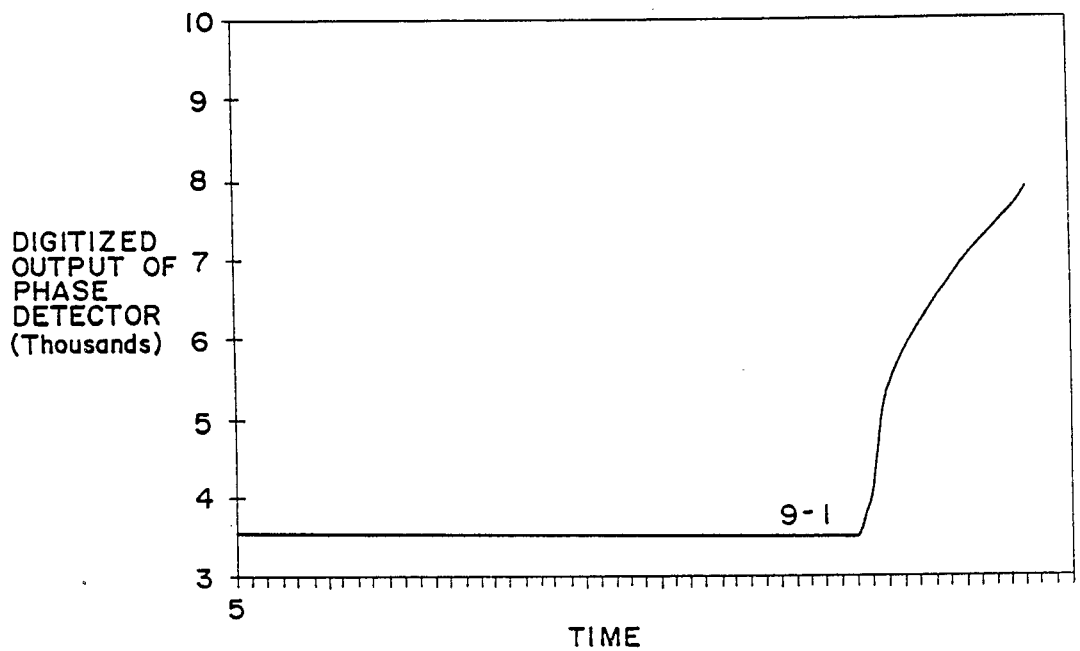
FIG. 9 illustrates the detection of $H_2O_2$ with a sintered pellet of tantalum having catalase over silicone.

FIG. 9 illustrates the effects of $H_2O_2$ on a pellet of tantalum having catalase on the surface of the pellet. At 9-1, the $H_2O_2$ was added and counts from the A/D converter show a dramatic decrease in capacitance. This decrease in capacitance is related to the concentration of $H_2O_2$ in the aqueous environment. In this experiment, 90% of the count increase occurs in 1-2 minutes

EXPERIMENT II

Detection of a Human Antibody with Biosensor Containing Immobilized Antigen

Planar capacitors were made on a 4-inch silicon wafer that had been thermally oxidized to produce a 1 micron insulating layer of $SiO_2$. 1 micron of Aluminum was deposited on the $SiO_2$ surface and then etched using standard photolithography techniques to produce an interdigitated pattern. The metal was then passivated with a 300 angstrom layer of $SiO_2$, followed by a 1,000 angstrom layer of $Si_3N_4$, followed by a final 300 angstrom layer of $SiO_2$. The final $SiO_2$ layer was added to facilitate the bonding of the coating. Wires were attached to the bonding pads of the chip with conductive epoxy (Transene Nickle Bond type 50) and the wire bonding area, chip sides and back were potted with a non-conductive epoxy (Emerson and Cuming, Stycast 2850FT with catalyst 9 or 24LV).

| | |
|---|---|
| Chip Thickness | 17 mils |
| Chip Length | 10 mm |
| Chip Width | 9 mm |
| Line Separation | 25 um |
| Structure Repeat Distance | 50 um |
| Finger Length | 8 mm |
| Finger Number | 125 |
| Baseline Capacitance | 2200–2300 pF |

Human Immunodeficiency Virus (HIV) core protein (p24) (Cytotech, 1 mg/ml in phosphate-buffered saline (PBS, pH 7.4)) was covalently attached with glutaraldehyde to the surface of an RTV silicone/APS-derivatized test sensor. Specifically, the sensors were coated with RTV silicone by dipping into 1% solution of silicone (GE RTV 118) in HPLC grade Acetone three times with air drying between each dip, and drying overnight at room temperature. Sensors were further coated with 3-aminopropyltriethoxy silane (APS) by dipping the RTV silicone-coated sensors for 2 minutes in a solution of 19 ml. 95% ethanol (containing methanol and isopropanol), 1 ml. deionized water and 400 mml. APS, followed by drying at room temperature overnight.

The RTV silicone/APS-coated sensors were soaked in phosphate-buffered saline pH 7.4 (PBS) at room temperature for 30–60 minutes to remove excess APS. 100 $\mu$l. of a 1:100 dilution in PBS of 25% glutaraldehyde was applied to the surface and the sensor was incubated for 1 hour at room temperature. After removing the glutaraldehyde solution, a solution containing 10 $\mu$g. HIV p24 in 100 $\mu$l. PBS was added to the test sensor. A solution containing 10 $\mu$g. human serum albumin (HSA) in 100 $\mu$l. PBS was added to the reference sensor and both sensors were incubated overnight at 4 degrees in a humidified chamber.

Figure 10:
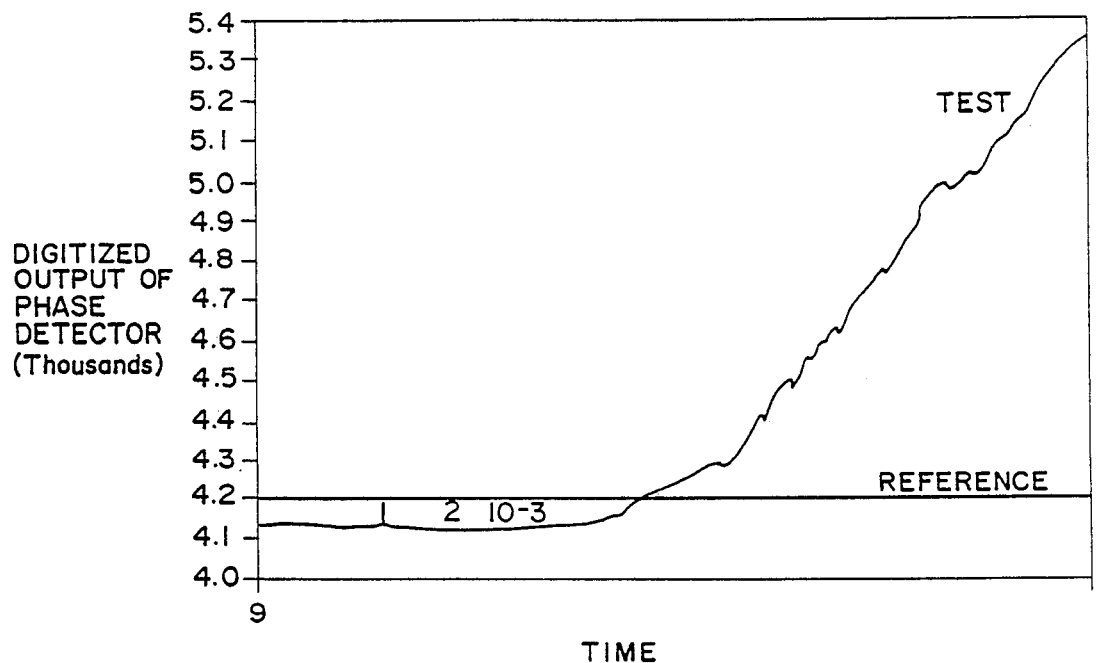
FIG. 10 illustrates the detection of HIV antibody with a planar capacitive sensor of FIG. 1.

Both test (p24) and reference (HSA) sensors were washed in PBS containing 0.05% HSA (PBS/HSA) and then soaked in a PBS/HSA solution for 1 hour. 120 $\mu$l of undiluted human plasma (ARC 70) (previously shown to contain antibodies against HIV proteins by EIA) was placed on top of both sensors, and they were incubated for 2 hours at room temperature. Both sensors were washed with PBS/HSA and then incubated with 100 $\mu$l of a solution of a complex of catalase and recombinant Protein G in PBS for 2 hours at room temperature. After a final wash with PBS/HSA, the sensors were placed in separate compartments of a Falcon microwell plate in 2 ml of PBS/HSA. As shown in FIG. 10 at 10-3, addition of 10 $\mu$l of 30% $H_2O_2$ caused an increase in the sensor response of the test (p24) but not the reference (HSA) sensor. In this experiment, 90% of the count increase occurs in 1–2 minutes and indicates that capacitance changed 10 pf in that time, approximately.

Protein G-catalase complexes were prepared by combining 3.6 mg bovine liver catalase with 10 $\mu$l of 0.25% glutaraldehyde in PBS and incubating at room temperature for 65 minutes. 100 $\mu$l of Protein G solution (1 mg in PBS) was added and incubation continued at room temperature for 65 minutes. 5 $\mu$l of 1 M ethanolamine was added to react with any excess glutaraldehyde, and incubation at room temperature was continued for 1 hour. The sample was then applied to a 1.5 cm diameter ×17.5 cm column of Sepharose 6B and eluted with PBS containing 0.01% sodium azide. The position of fractions containing catalase was determined from the optical density at 405 nm. Fractions from the leading edge of the catalase monomer peak were used in the sensor experiments.

EXPERIMENT III

Detection of $H_2O_2$ with a Biosensor Having Immobilized Catalase in the Presence of a Poison Two tantalum pellets were prepared as in the previous Experiment II. They were then soaked in 2 $\mu$l of PBS containing 450 $\mu$g catalase for 2 hours at room temperature. The excess catalase was rinsed off by soaking the tantalum pellets in PBS for 1 hour at room temperature. The pellets were then placed in 2 $\mu$l PBS and connected to the phase sensitive detector. 25 mM $H_2O_2$ was added.

The assembly was removed and put into 2 $\mu$l of fresh PBS. 25 mM $H_2O_2$ was added immediately, followed by 250 ppm $NaN_3$.

Figure 11:
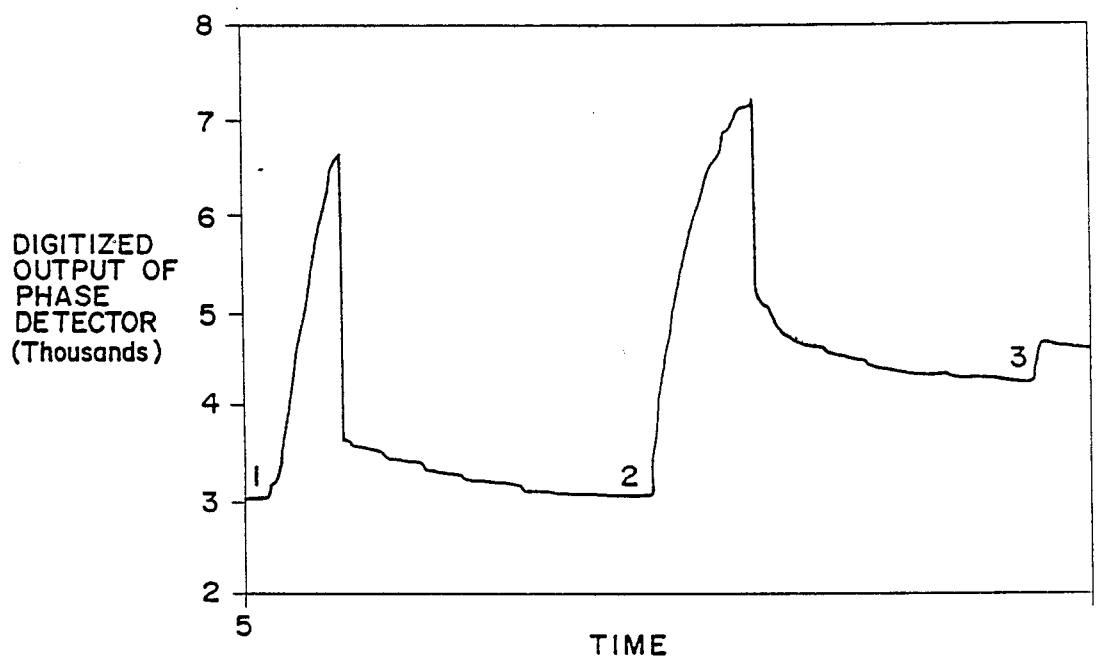
FIG. 11 illustrates the detection of poison with a sintered pellet of tantalum having catalase over silicone.

FIG. 11 illustrates the effects of $H_2O_2$ on a pellet of tantalum having catalase on the surface of the pellet and in the presence of a poison to catalase. At 11-1, $H_2O_2$ was added and counts from the A/D converter increased dramatically, indicating a dramatic decrease in capacitance. The pellets were placed in PBS and the counts decreased dramatically because nucleated bubbles were removed from the surface and no more bubbles nucleate at the surface. At 11-2, $H_2O_2$ was again added and an counts from the A/D converter increased dramatically, indicating another a dramatic decrease in capacitance. The pellets were placed in PBS and the counts again decreased dramatically. $H_2O_2$ was again added at 11-3, and immediately thereafter, a poison to the enzyme, 250 ppb of $NaN_3$, was added. The graph initially begins to rise as catalase begins to form bubbles. However, upon the addition of the $NanN_3$, the catalase is poisoned and the graph plateaus at the value caused by the small amount of bubbles formed. In this experiment, 90% of the count increase occurs in 1–2 minutes and indicates that capacitance changed 20 pf in that time, approximately.

The following gas producing enzymes are preferred for the embodiments of this invention.

Enzyme

1. Catalase
2. Urease

3. Decarboxylases
L-Arginine Decarboxylase
L-Glutamic Decarboxylase
L-Histidine Decarboxylase
L-Ornithine Decarboxylase
Oxalate Decarboxylase
L-Phenylalanine Decarboxylase
L-Tyrosine Decarboxylase
Pyruvate Decarboxylase 4. Aspartase The sensor of this invention can sense anything that would modulate the $H_2O_2$ concentration in an aqueous environment. For example, HOCl (hypochlorous acid) destroys $H_2O_2$, so the sensor would not grow bubbles in the presence of HOCl ($+H_2O_2$). also, Glucose and $O_2$ produces Gluconolactone and this reaction is catalyzed by the enzyme glucose oxidase. Since $H_2O_2$ is also a product, a mixture of glucose and glucose oxidase and $O_2$ produces more $H_2O_2$ which would be converted to $O_2$ bubbles on the surface of the sensor.

The sensor can comprise other embodiments. The sensor surface can comprise an optical or acoustic waveguide. Nucleation of bubbles on the surface of such a waveguide would drastically alter the transmission of light by an optical fiber, light source, reflector or photo-detector to the transmission of acoustic waves by a piezoelectric crystal or waveguide, for instance. The surface upon which bubbles nucleate can comprise other materials as described in U.S. Pat. No. 4,748,882 for Capacitive Chemical Sensor For Detecting Certain Analytes, Including Hydrocarbons In A Liquid Medium, to Stanbro et al., the specification of which is incorporated by reference. Certain living organisms, such as yeast and bacteria, also produce gases that can be nucleated as bubbles. Modulation of the system is also accomplished with changes in pressure or temperature. DNA or RNA molecules could be bound to the sensor surface to test for the presence of DNA or RNA molecules in a test fluid.

Each embodiment of this invention concerns an enzyme and a substrate that chemically produce a volatile material. The volatile material changes phase and nucleates as bubbles. The nucleated bubbles form a gas bubble near a sensor surface. The gas bubble displaces a large volume of solution from adjacent the sensor surface, which drastically changes the dielectric properties of that sensor.

I claim:

1. Apparatus for sensing a biochemical analyte comprising:
   a sensor element having surface means which nucleate bubbles from volatile material;
   producing means for producing a volatile material in an amount dependent on a concentration of the biochemical analyte, said producing means including an enzyme and having a portion bound to the surface means; and
   wherein said surface means is adjacent to the producing means; and further comprising
   detection means adjacent the surface means for responding to the bubbles that nucleate on the surface means and which provides an output which is indicative of the concentration of the biochemical analyte.

2. The apparatus of claim 1, further comprising binding means bound to said producing means so as to modulate activity of said producing means.

3. The apparatus of claim 2, wherein said binding means is bound to the enzyme so as to sterically hinder the enzyme.

4. The apparatus of claim 1, wherein said producing means is bound to said surface means by binding means.

5. The apparatus of claim 4, wherein said binding means comprises an antibody and is conjugated to the enzyme.

6. The apparatus of claim 4, further comprising a human antibody, which is bound to the binding means.

7. The apparatus of claim 4, wherein said binding means comprises binding agents selected from the group consisting of antibodies, lectins, enzymes, and neural receptors.

8. The apparatus of claim 4, wherein said binding means binds comprises an immobilized analyte.

9. The apparatus of claim 4, wherein said binding means binds comprises an antigen and a human antibody.

10. The apparatus of claim 4, wherein said binding means comprises immobilized analyte at said surface means.

11. The apparatus of claim 10, wherein said immobilized analyte is selected from the group consisting of antigens, haptens, polysaccharides, glycoproteins, glycolipids, enzyme inhibitors, neurotransmitters, and hormones.

12. A capacitive sensor comprising:
    two electrodes;
    a passivation layer between the two electrodes, said passivation layer having surface means which nucleate bubbles from volatile material;
    producing mean for producing a volatile material in an amount dependent on a concentration of a biochemical analyte, said producing means including an enzyme and having a portion bound to the surface means; and
    wherein said surface means is adjacent to the producing means so as to nucleate bubbles between the two electrodes and change the dielectric properties of the sensor according to the nucleating bubbles.

13. The sensor of claim 12 further comprising binding means bound to the producing means so as to modulate activity of the producing means.

14. The sensor of claim 12, wherein the surface means comprises silicone rubber.

15. The sensor of claim 14, wherein the enzyme comprises catalase.

* * * * *